United States Patent
Swiecicki et al.

(10) Patent No.: US 7,322,472 B2
(45) Date of Patent: Jan. 29, 2008

(54) VOID VOLUME INDICATOR AND METHOD OF CONSUMER PRODUCT SELECTION

(75) Inventors: Alethea Angelic Marie Swiecicki, Greenville, WI (US); David Charles Musil, Appleton, WI (US); Debra Ann Haase, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 741 days.

(21) Appl. No.: 10/251,500

(22) Filed: Sep. 20, 2002

(65) Prior Publication Data

US 2004/0055367 A1  Mar. 25, 2004

(51) Int. Cl.
*B65D 85/00* (2006.01)
(52) U.S. Cl. .................................. 206/459.1
(58) Field of Classification Search ............. 206/459.1, 206/459.5, 440, 494; 116/206
See application file for complete search history.

(56) References Cited

U.S. PATENT DOCUMENTS

| | | | |
|---|---|---|---|
| 3,633,581 | A | 1/1972 | Welch |
| 3,871,231 | A | 3/1975 | Ciarico |
| 4,834,733 | A | 5/1989 | Huntoon et al. |
| 5,121,630 | A | 6/1992 | Calvin |
| 5,219,341 | A | 6/1993 | Serbiak et al. |
| 5,354,289 | A | 10/1994 | Mitchell et al. |
| 5,356,398 | A | 10/1994 | Willis |
| H1376 | H | 11/1994 | Osborn, III et al. |
| 5,647,863 | A | 7/1997 | Hammons et al. |
| 5,807,362 | A | 9/1998 | Serbiak et al. |
| 5,839,585 | A | 11/1998 | Miller |
| 5,865,322 | A | 2/1999 | Miller |
| 5,947,302 | A | 9/1999 | Miller |
| 6,063,042 | A | 5/2000 | Navot et al. |
| 6,093,027 | A | 7/2000 | Unger et al. |
| 6,284,942 | B1 | 9/2001 | Rabin |
| 6,318,555 | B1 | 11/2001 | Kuske et al. |
| 6,454,095 | B1 * | 9/2002 | Brisebois et al. ........... 206/494 |
| 6,601,705 | B2 * | 8/2003 | Molina et al. ............... 206/494 |

(Continued)

FOREIGN PATENT DOCUMENTS

EP  0 776 645 A1  6/1997

(Continued)

OTHER PUBLICATIONS

Patent Cooperation Treaty Search Report from the International Search Authority, International Application No. PCT/US 03/25639 dated Apr. 6, 2004.

*Primary Examiner*—Hezron Williams
*Assistant Examiner*—John Fitzgerald
(74) *Attorney, Agent, or Firm*—Ralph H. Dean; Randall W. Fieldhack

(57) ABSTRACT

A void volume indicator, a packaging system, and a method of consumer product selection are disclosed. The void volume indicator can have either a primary wetness indicator, a secondary wetness indicator, or both that corresponds to a portion of a package having either a primary capacity indicator, a secondary capacity indicator, or both. After using the void volume indicator, feedback from the indicator can be used to select an absorbent article having an appropriate absorbent capacity for the person's needs.

13 Claims, 6 Drawing Sheets
(5 of 6 Drawing Sheet(s) Filed in Color)

U.S. PATENT DOCUMENTS

| | | | |
|---|---|---|---|
| 6,685,020 B2 * | 2/2004 | Briseboi et al. | 206/440 |
| 6,763,944 B2 * | 7/2004 | Ronn et al. | 206/440 |
| 2002/0148749 A1 | 10/2002 | Briseboi et al. | |

FOREIGN PATENT DOCUMENTS

| EP | 0 986 996 A2 | 3/2000 |
|---|---|---|
| EP | 1 153 838 A1 | 11/2001 |
| EP | 1 221 312 A2 | 7/2002 |
| EP | 1 306 069 A2 | 5/2003 |
| WO | WO97/45088 A1 | 12/1997 |
| WO | WO 01/52126 A2 | 7/2001 |
| WO | WO 01/75771 A1 | 10/2001 |
| WO | WO 01/95845 A1 | 12/2001 |
| WO | WO 02/03902 A2 | 1/2002 |
| WO | WO 02/07661 A2 | 1/2002 |
| WO | WO 02/30347 A1 | 4/2002 |
| WO | WO 02/055788 A2 | 7/2002 |
| WO | WO 03/053279 A2 | 7/2003 |

* cited by examiner

VOID VOLUME INDICATOR AND METHOD OF CONSUMER PRODUCT SELECTION

BACKGROUND

Currently, absorbent articles are packaged in a wide variety of packages that employ numerous confusing methods to indicate different absorbent capacities to the consumer. While the manufacturers of such products have been adept at providing an adequate selection of absorbent products having different levels of absorbency, they have had less success in educating the consumer as to which product is appropriate for their needs. In particular, degrees of incontinence and void volumes for individuals vary from light infrequent episodes to chronic heavy amounts. Currently, consumers are left to a "trial and error" approach to selecting an appropriate absorbent article. They must buy a product having a particular absorbency level, try the product to determine if either leakage occurs or under utilized capacity is present, and then reselect another absorbency level having either a higher or lower absorbency depending on the previous results until the appropriate product for their needs is found. Such a process can be time consuming at best, or worse, it can alienate the consumer from ever using that brand of absorbent article again if the failure on the first attempt was catastrophic.

Therefore, what is needed is a method of determining a person's degree of incontinence and recommending an absorbent article having an appropriate absorbent capacity for their needs. In addition, what is needed is a void volume indicator that indicates an appropriate absorbency level for a person's degree of incontinence.

SUMMARY

It has been determined that the above needs can be met by providing a void volume indicator, which instead of measuring a specific volume of fluid, is coded to correspond with an absorbent article package containing absorbent articles having an appropriate capacity for the measured void volume.

In one aspect, the invention resides in a void volume indicator including a plurality of wetness indication zones each having a primary wetness indicator, and where the plurality of wetness indication zones provide feedback by the primary wetness indicators to indicate progressively increasing void volumes. The primary wetness indicators each having a color, and the color corresponds to a package color located on at least a portion of a package containing at least one absorbent article having an absorbent capacity appropriate for the indicated void volume.

In another aspect, the invention resides in a void volume indicator including a plurality of wetness indication zones each having a secondary wetness indicator, and where the plurality of wetness indication zones provide feedback by the secondary wetness indicators to indicate progressively increasing void volumes. The secondary wetness indicators each having an indicia, and the indicia correspond to a package indicia located on at least a portion of a package containing at least one absorbent article having an absorbent capacity appropriate for the indicated void volume.

In another aspect, the invention resides in a packaging system including a plurality of packages each containing at least one absorbent article having an absorbent capacity, each of the packages contain only absorbent articles having the same absorbent capacity, and at least two packages contain absorbent articles having a different absorbent capacity. An exterior face located on each package having a primary capacity indicator, and the primary capacity indicators are different color hues of the same base color. A darker hue is present on the package containing the absorbent article having a higher absorbent capacity than the package containing the absorbent article having a lower absorbent capacity.

In another aspect, the invention resides in a method of absorbent article selection including: providing a void volume indicator; providing a plurality of packages each containing at least one absorbent article having an absorbent capacity, each of the packages contain only absorbent articles having the same absorbent capacity, and at least two packages contain absorbent articles having a different absorbent capacity; and recommending the absorbent article having the absorbent capacity indicated after using the void volume indicator.

In another aspect, the invention resides in a method of absorbent article selection including: using a void volume indicator, capturing bodily fluids with the void volume indicator, and selecting an absorbent article package based on feedback from the void volume indicator.

In another aspect, the invention resides in an absorbent article including a transparent bottomsheet, and an absorbent structure disposed adjacent the transparent bottomsheet.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above aspects and other features, aspects, and advantages of the present invention will become better understood with regard to the following description, appended claims, and accompanying drawings where:

DETAILED DESCRIPTION

As used herein "color hues of the same base color" means that the different colors are obtained by adding various amounts of a black pigment to the base color commonly called a shade, or the different colors are obtained by adding various amounts of a white pigment to the base color commonly called a tint.

As used herein "corresponds" means to be consistent, similar, or comparable. It is not necessary for the two corresponding items to be identical or to match. For instance, indicia having the same shape, but of two differing sizes are considered corresponding.

Figure 1:
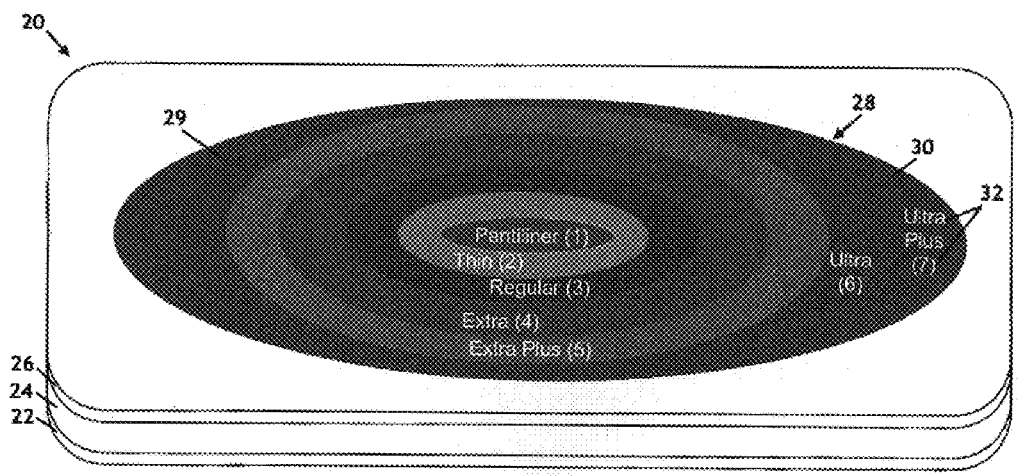
FIG. 1 illustrates one embodiment of the void volume indicator.

Referring now to FIG. 1, one embodiment of a void volume indicator 20 is illustrated. In this embodiment, the void volume indicator is in the form of a specially designed absorbent pad that includes a bottomsheet 22, and an absorbent structure 24. If desired, a topsheet 26 can be included.

Various types of absorbent articles are known to those of skill in the art, and suitable materials for the bottomsheet, topsheet, and absorbent structure are readily known or can be obtained from reading patents relating to absorbent articles. For instance, the topsheet can be a spunbond nonwoven, the absorbent structure can be a cellulose fluff/superabsorbent mixture, and the bottomsheet can be a polyethylene film. In addition, it is possible to design the pad with other features known to those of skill in the art such as wings, elastic members, body fitting shapes, multiple absorbent layers, intake/distribution layers, tissue layers, or attachment mechanisms to either the body or undergarments as illustrative non-exhaustive possibilities.

The void volume indicator includes a plurality of wetness indication zones 28, in this instance concentric ovals 29, which correspond to increasing void volumes that are absorbed by the pad. For instance, pouring about 5 ml of urine or fluid into the center of the pad will cause the pad to wet only the oval identified as "Pantiliner or 1". Pouring about 50 ml of urine into the center of the pad with cause the pad to wet out to the oval identified as "Extra Plus or 5." The pad's wicking rate is controlled by the design of the absorbent structure 24 such that a specific fluid capacity is absorbed by each wetness indication zone 28 before wicking proceeds to the next zone.

One such method to control the wicking would be to vary the thickness or density of the absorbent structure 24 in each of the wetness indication zones 28 to control the absorbent capacity for that zone. Thus, the absorbent structure would be thinner or less dense towards the pad's center and thicker or denser towards the pad's periphery. Another technique would be to vary the ratio of pulp to superabsorbent particles present in each wetness indication zone. Those of skill in the art know or can determine the relative absorbent properties of materials commonly used for an absorbent structure such that designing the pad to wet or wick to a specific region for a given fluid volume is possible.

Figure 2:
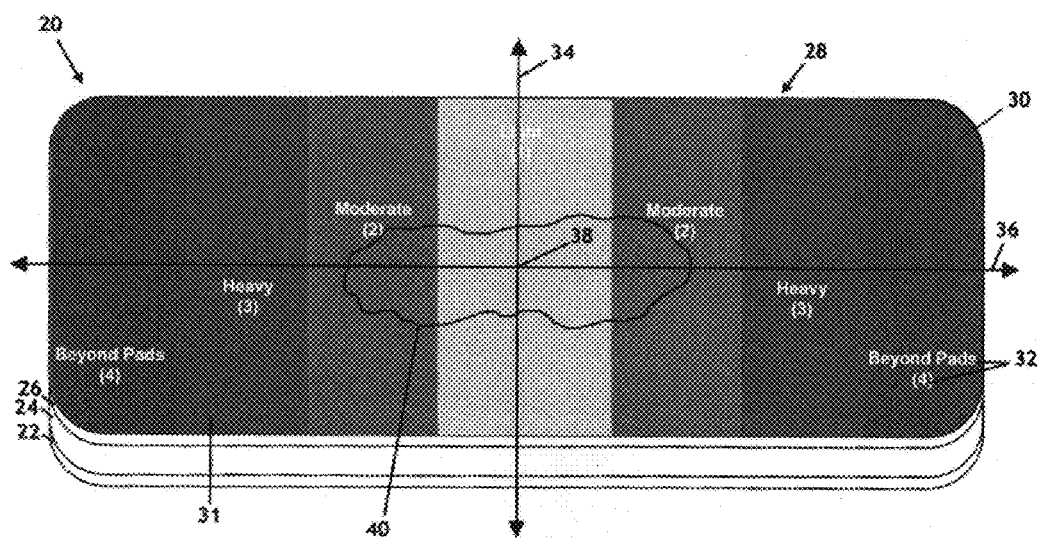
FIG. 2 illustrates another embodiment of the void volume indicator.
Figure 3:
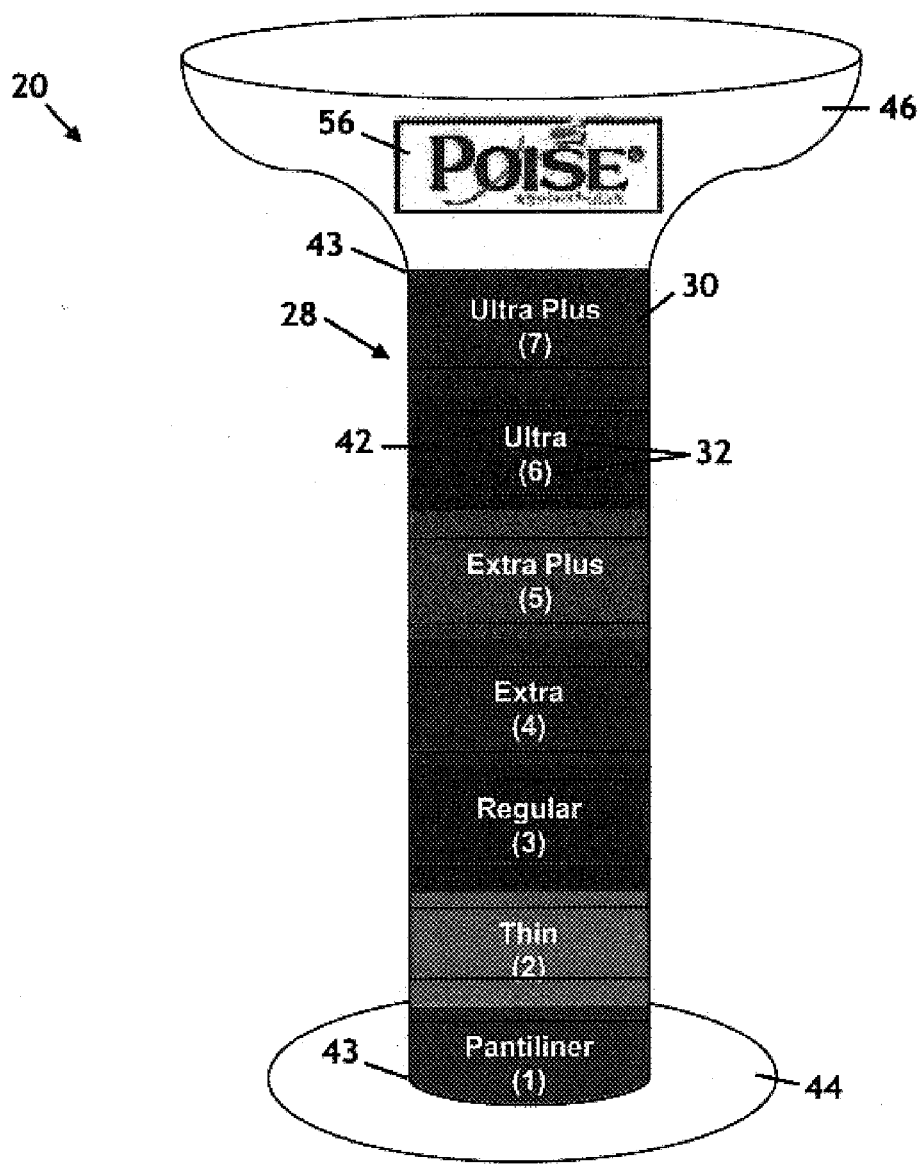
FIG. 3 illustrates another embodiment of the void volume indicator.
Figure 4:
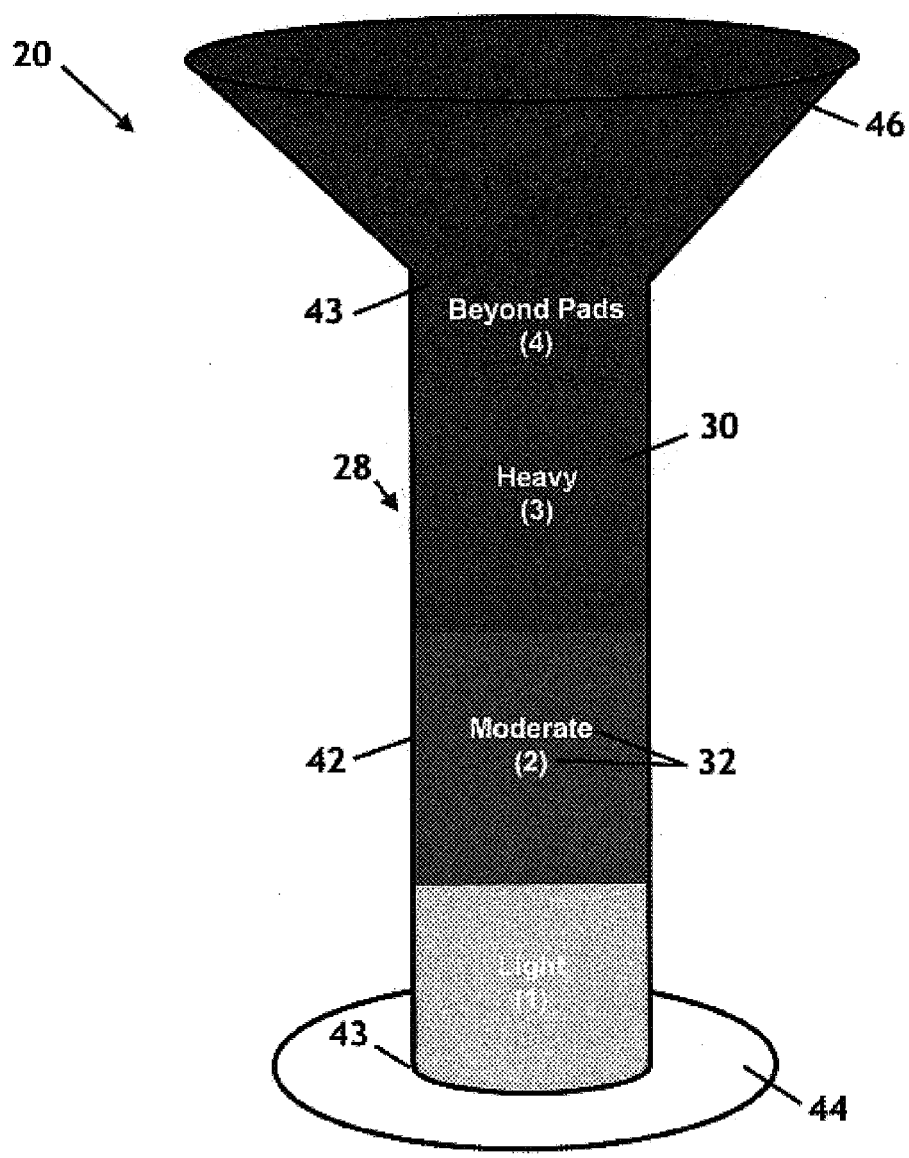
FIG. 4 illustrate another embodiment of the void volume indicator.

The number of wetness indication zones 28 provided will depend on how many different absorbent capacities are sold by the manufacturer for a specific product line. Referring to FIGS. 1 and 3, the void volume indicator 20 has seven wetness indication zones. Referring to FIGS. 2 and 4, the void volume indicator 20 has four wetness indication zones. The table below indicates two possible methods for assigning the fluid capacity in milliliters to the wetness indication zones. As seen in the table, it is possible to design the ranges to either overlap or to be distinct. Overlapping ranges have been found to provide a benefit when not all absorbency levels are stocked by a retailer.

TABLE 1

Wetness Indication Zones and Corresponding Absorbent Capacity

| FIGS. 1 and 3 | | FIG. 2 and 4 | |
| --- | --- | --- | --- |
| Pantiliner or 1 | 0–14 ml | Light or 1 | 0–30 ml |
| Thin or 2 | 9–27 ml | Moderate or 2 | 31–60 ml |
| Regular or 3 | 16–37 ml | Heavy or 3 | 61–90 ml |
| Extra or 4 | 25–59 ml | Beyond Pads or 4 | >90 ml |
| Extra Plus or 5 | 35–71 ml | | |
| Ultra or 6 | 43–80 ml | | |
| Ultra Plus or 7 | 51–95 ml | | |

Referring back to FIG. 1, each wetness indication zone 28 contains a primary wetness indicator 30, and a secondary wetness indicator 32. The primary wetness indicator 30 is a color. The secondary wetness indicator 32 is indicia such as words, numbers, letters, or symbols. The terms Primary and Secondary should not be read as limiting in that it is possible to design the void volume indicator 20 with only a primary wetness indicator 30, with only a secondary wetness indicator 32, or with both a primary and secondary wetness indicator (30, 32) as shown. Unlike other volume measuring devices instead of indicating a specific volume of fluid in milliliters or other volumetric unit, the void volume indicator 20 identifies an appropriate absorbent capacity for an absorbent article that is sold by a manufacturer. Thus, a consumer can use the void volume indicator 20 for a period of time capturing the episodes of incontinent urine leakage, and then the consumer can remove the indicator and readily determine which capacity to select when buying an absorbent article. Alternatively, the consumer can determine that an absorbent pad has insufficient capacity, and they need to buy larger capacity products such as briefs or underwear type absorbent articles. (FIGS. 2, 4)

The primary wetness indicators 30 can be various colors such as white, pink green, blue, etcetera. Alternatively, the primary wetness indicators can be various colors corresponding to different color hues of the same base color. For instance, the colors could be a progression from very light blue to very dark blue. It has been determined that consumers prefer hues of one base color progressing from light to dark to indicate absorbent capacities from low to high. This is less confusing than trying to remember an arbitrary assignment of one color, such as green, to low capacity and another color, such as purple, to high capacity. The primary wetness indicators 30 for each absorbent capacity utilized on the void volume indicator 20 can be placed onto at least a portion of a corresponding absorbent article package containing absorbent articles having an absorbent capacity appropriate for the indicated void volume.

The primary wetness indicators 30 can be placed onto the bottomsheet 22, the absorbent structure 24, or the topsheet 26 of the pad by coloring the appropriate area of that component. In a desirable configuration, the bottomsheet 22 is transparent such as a transparent plastic or film. A stabilized or cross linked absorbent material containing cellulose fibers, a bonding agent such thermoplastic fibers, and a superabsorbent is used for the absorbent structure. An example of a stabilized absorbent material is disclosed in PCT application WO 02/055788 A2 entitled "Cellulosic Product Having High Compression Recovery." In general, stabilized absorbent structures are white, and the corresponding colored primary wetness indications zones 30 can be printed or otherwise contained on or by the absorbent structure, such as by dying the pulp. After use, it is a relatively simple operation to turn the pad over and view the wetting pattern through the transparent bottomsheet 22 to determine the recommended absorbent product having the necessary absorbent capacity. If desired, the transparent bottomsheet 22 could have the colored pattern present on it instead.

The secondary wetness indicators 32 are indicia such as words, numbers, letters, or symbols that correspond to the absorbent articles having different absorbent capacities. It has been determined that consumers prefer numbers instead of words, since this is more intuitive especially when a lower number is used for a low capacity and a higher number is used for a higher capacity. For instance, remembering that a "4" has lower capacity than a "6" is easier than trying to remember an "Extra" has less capacity than an "Ultra". The secondary wetness indicators 32 for each absorbent capacity utilized on the void volume indicator 20 can be placed onto at least a portion of a corresponding absorbent article package containing absorbent articles having an absorbent capacity appropriate for the indicated void volume.

The indicia can be placed onto the bottomsheet 22, the absorbent structure 24, or the topsheet 26 of the pad by printing (or other means) the appropriate area of that component. In addition, it is not required to place the primary and secondary wetness indicators (30, 32) onto the same component. For example, if a transparent bottomsheet is used the absorbent structure can be colored while the indicia can be printed onto the bottomsheet.

Referring now to FIG. 2, another embodiment for the void volume indicator 20 is shown. This embodiment is similar to FIG. 1, but instead of the wetness indication zones 28 being concentric ovals 29, the wetness indication zones are rectangular areas 31. The rectangular areas 31 are orientated such that their length is parallel to a transverse central axis 34 and their width is parallel to a longitudinal central axis 36. The void volume indicator 20 works by wicking urine and other fluids progressively farther away from a center 38 where ideally the insult occurs. Since the wicking or the insult may not occur perfectly uniformly, a wetness indication line 40 after the urine insult can assume the non-uniform shape as drawn. A non-uniform wetness line can be confusing to read on the void volume indicator depicted in FIG. 1, since the line 40 could wander or cross into several wetness zones 28. The illustrated void volume indicator solves this problem by use of the rectangular areas 31. As indicated in the figure, a "Moderate or 2" absorbent capacity is appropriate for this occurrence by examining the longitudinal ends of line 40.

Referring now to FIGS. 3 and 4, another embodiment of the void volume indicator 20 is shown. In this configuration, the void volume indicator includes a hollow cylinder 42 having a pair of opposing ends 43. A base 44 is attached to one opposing end, and a funnel shaped opening 46 is attached to the other opposing end. The hollow cylinder 42 is marked with a plurality of wetness indication zones 28 each, having a primary wetness indicator 30 and a secondary wetness indicator 32. Desirably, the hollow cylinder 42 is transparent and the primary wetness indicators 30 are colored bands around the cylinder's periphery. Alternatively, the primary wetness indicators could be a colored line or bar.

The void volume indicator of FIGS. 3 and 4 can be utilized by individuals who are partially continent to assess their needed absorbent capacity. Alternatively, the void volume indicator can be graduated with common volumetric graduations in addition to the primary and secondary wetness indicators (30, 32) for use by hospitals. It is known that individuals recovering from prostate surgery are generally Incontinent immediately following surgery, and often many hospitals will monitor a patient's urine output while using a catheter after surgery. By use of the void volume indicator, the hospital could obtain its required volumetric reading, and the patient would know what absorbent article capacity was required to be purchased after removal of the catheter.

Figure 5:
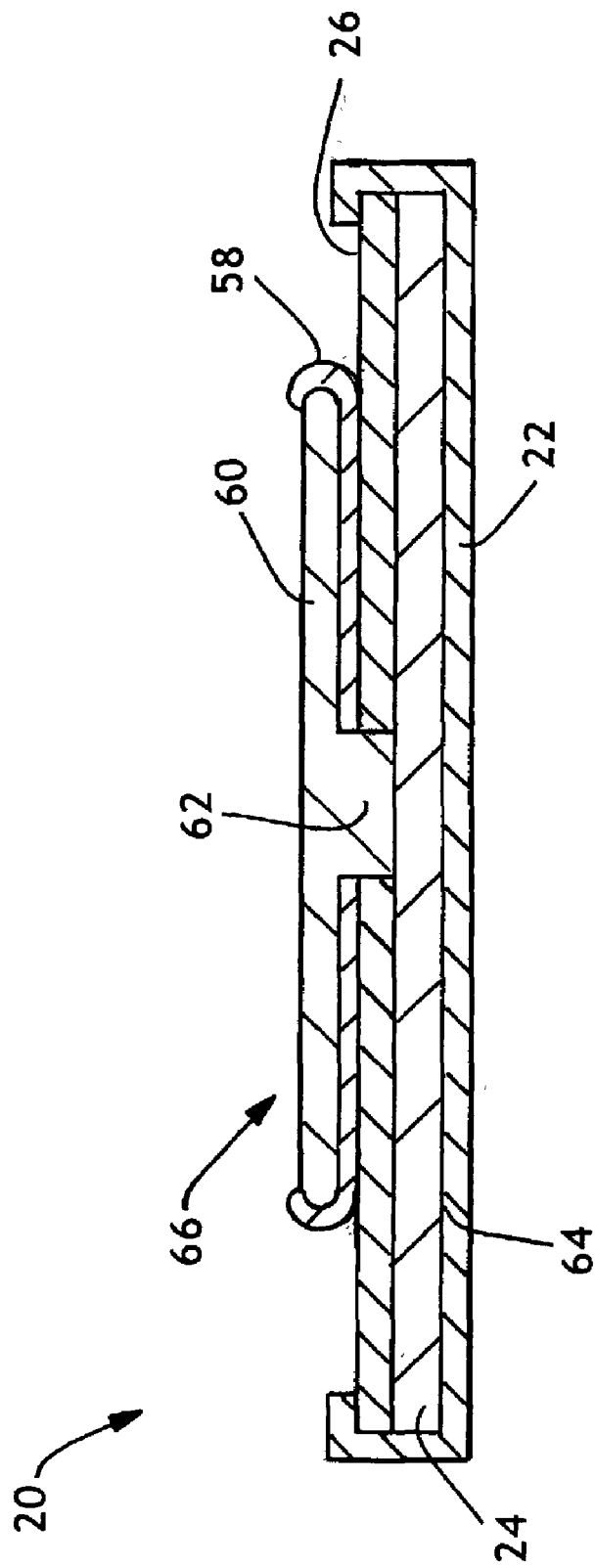
FIG. 5 illustrates another embodiment of the void volume indicator.

Referring now to FIG. 5 another void volume indicator 20 is shown as a cross-section through its longitudinal central axis. The indicator includes a transparent bottomsheet 22, an absorbent structure 24, and a topsheet 26. The bottomsheet can overlap the topsheet along the sides and ends of the indicator as shown. Desirably, the absorbent structure is a stabilized absorbent and has the wetness zones 28 of FIG. 1 present on its lower surface 64. Alternatively, the wetness zones can be present on the bottomsheet.

An intake member 66 having a baffle 58 partially surrounding an intake/distribution material 60 is disposed on the topsheet 26. If desired, an additional topsheet 26 can be disposed over the intake/distribution material 60 (not shown). The intake member 66 can be round when viewed from the top, and it can cover less surface area than the topsheet 26 on which it is disposed. If desired, the intake member 66 can be an oval, elliptical, or other shape that is comfortable against the body.

The function of the intake member 66 is to collect and control the release fluid through an orifice 62 into the absorbent structure 24. The baffle 58 is a liquid impermeable material, or is treated to be liquid impermeable, such that fluid or urine 35 present in the intake member 66 must pass through the orifice 62 to enter the absorbent structure 24, instead of passing through the baffle 58 and the topsheet 26.

The intake member 66 increases the accuracy of the void volume indicator by eliminating centering and alignment issues when using the void volume indicator of FIG. 1, because the collected fluid enters the absorbent structure through the orifice. Because the orifice 62 can be precisely aligned with the center of the wetness zones, instances of fluid wetness patterns not coincident with the center of the wetness zones are reduced.

Suitable materials for the topsheet, bottomsheet, absorbent structure, baffle, and intake/distribution material are known to those of skill in the art. For example, the topsheet can be a spunbond nonwoven, the bottomsheet a polyethylene film, the baffle a polyethylene film, and the intake/distribution material a PRISM nonwoven material available from Kimberly-Clark Corporation having an office in Neenah, Wis.

Figure 6:
FIG. 6 illustrates absorbent article packages of the present invention.

Referring now to FIG. 6, a plurality of packages 48 with each package containing absorbent articles having a different absorbent capacity is shown. An exterior face 50 of each package can include a portion having a primary capacity indicator 52 and another portion having a secondary capacity indicator 54. The package 48 also has a brand/product indicator 56 to convey that it contains a specific type of absorbent article from a specific manufacture. The primary and secondary absorbent capacity indicators (52, 54) correspond in color or indicia to the primary and secondary wetness indicators (30, 32) on the void volume indicator 20 (FIGS. 2 and 4). The terms Primary and Secondary should not be read as limiting in that it is possible to design the packages 48 with only a primary capacity indicator 52, with only a secondary capacity indicator 54, or with both a primary and secondary capacity indicator (52, 54) as shown.

As seen in the illustration, utilization of a primary capacity indicator 52, which has various color hues of the same base color, readily conveys an increasing level of absorbency for the packages. A lighter hue is used for the package containing the lowest absorbent capacity products, while a darker hue is used for the package containing the highest absorbent capacity products. The absorbent capacities for the different packages is further enhanced by use of the secondary capacity indicator 54 superimposed over the primary capacity indicator 52. The primary capacity indicator 52 can be in the shape of a rectangular bar 57 orientated horizontally on the exterior face 50. Alternatively, the color hue could be the whole package, a vertical bar, or other portion of the exterior face.

The void volume indicator 20 and corresponding packages 48 can be used jointly to provide a method for consumer product selection. Initially, the consumer determines that they have an incontinence problem and makes a determination as to the type of product they wish to use. For instance, they may wish to initially select an absorbent pad type product for use with conventional underwear as opposed to a brief type product that would replace their underwear. Next, the consumer would be provided with a void volume indicator 20 having its associated wetness indicators (30, 32) that correspond to the package capacity indicators (52, 54) for the type of product the consumer desires to use. If desired, the brand/product indicator 56 can be placed onto the void volume indicator 20 (FIG. 3) to help ensure consumers understand the void volume indicator is for the type of product they desire to use. The consumer then uses the void volume indicator under the conditions they desire for a product recommendation. For instance, they may use it during active periods, or during overnight conditions, for which the results and required absorbent capacity could vary. The indicated absorbent capacity and hence the recommended product is determined from the void volume indicator 20 after use. From this information, the consumer knows what range or specific product they should select. Thus, when shopping it is a simple matter to select the packaging corresponding to the results obtained with the void volume indicator to purchase absorbent articles with the necessary absorbent capacity.

The void volume indicator results should be viewed more as a recommendation, since the consumer may select a different absorbent capacity based on other factors besides the product's absorbent capacity. For example, one size may fit better, they may prefer more capacity than required for extra security, they may prefer other product features, or the price may enter into the selection decision. Alternatively, the consumer may choose a higher absorbency to gain a longer wearing time in order to minimize the number of changes required during the day. For example, a consumer who uses the void volume indicator of FIG. 1 and who falls into the "Extra or 4" range may wish to consider using the "Extra Plus or 5" pad or the "Regular or 3" pad instead for the above reasons.

While the void volume indicator has been described for use by incontinent persons in conjunction with the capturing of urine, the indicator can be used to capture other bodily fluids such as menses, and for the selection of a sanitary napkin. It will be appreciated that the foregoing description, given for the purposes of illustration, is not to be construed as limiting the scope of the invention, which is defined by the claims and all equivalents thereto.

We claim:

1. A packaging system comprising:
   a plurality of packages each containing at least one absorbent article having an absorbent capacity, each of the packages contains only absorbent articles having the same absorbent capacity, and at least two packages contain absorbent articles having a different absorbent capacity;
   an exterior face located on each package comprises a primary capacity indicator wherein the primary capacity indicator on each package comprises a different color hue of the same base color, and a darker hue is present on a package containing an absorbent article having a higher absorbent capacity than a package containing an absorbent article having a lower absorbent capacity; and
   a void volume indicator, wherein the primary absorbent capacity indicator on each package corresponds to a plurality of primary wetness indicators located on the void volume indicator.

2. The package system of claim 1, wherein the void volume indicator comprises a plurality of wetness indication zones, each zone comprising a primary wetness indicator, the plurality of wetness indication zones each provide feedback by the primary wetness indicator to indicate progressively increasing void volumes.

3. The package system of claim 1, wherein the void volume indicator comprises a hollow cylinder having a base located on one end and a funnel shaped opening located on an opposing end, and wherein the primary wetness indicators comprise colored areas disposed on the cylinder between the base and the funnel shaped opening.

4. The packaging system of claim 1 further comprising a secondary capacity indicator having an indicia selected from the group consisting of words, numbers, letters, or symbols, and the secondary absorbent capacity is located on the exterior face of each package.

5. The packaging system of claim 4 wherein the primary absorbent capacity indicator comprises a rectangular bar and the secondary capacity indicator is superimposed over the primary absorbent capacity indicator.

6. The package system of claim 4 wherein the indicia are selected from the group consisting of Pantiliner, Thin, Regular, Extra, Extra Plus, Ultra, Ultra Plus, and Beyond Pads.

7. The package system of claim 4 wherein the indicia are selected from the group consisting of Light, Moderate, Heavy, and Beyond Pads.

8. The package system of claim 4 wherein tile indicia are selected from the group consisting of 1, 2, 3, 4, 5, 6, 7, 8, 9, and 10, and wherein a higher numeral represents an increasing void volume.

9. The package system of claim 1, wherein the void volume indicator comprises an absorbent pad having an absorbent structure disposed on a bottomsheet, and wherein the primary wetness indicators comprise colored areas of the absorbent pad.

10. The package system of claim 9 wherein the colored areas are concentric ovals.

11. The package system of claim 9 wherein the void volume Indicator further comprises a central longitudinal axis and a central traverse axis, the colored areas comprising rectangular areas having a longitudinal width dimension and a traverse length dimension, and wherein the length dimension is greater than the width dimension.

12. The package system of claim 9 wherein the bottomsheet is transparent.

13. A packaging system comprising:
   a plurality of packages each containing at least one absorbent article having an absorbent capacity, each of the packages contains only absorbent articles having the same absorbent capacity, and at least two packages contain absorbent articles having a different absorbent capacity;
   an exterior face located on each package comprises a primary capacity indicator; wherein the primary capacity Indicator on each package comprises a different color hue of the same base color, and a darker hue is present on a package containing an absorbent article having a higher absorbent capacity than a package containing an absorbent article having a lower absorbent capacity
   a void volume indicator, wherein the primary absorbent capacity indicator on each package corresponds to a plurality of primary wetness indicators located on the void volume indicator; and
   a secondary capacity indicator having an indicia selected from the group consisting of words, numbers, letters, or symbols, and the secondary absorbent capacity is located on the exterior face of each package
   wherein the primary and the secondary absorbent capacity indicators on each package corresponds to a plurality of primary and a plurality of secondary wetness indicators located on a void volume indicator.

* * * * *